(12) United States Patent
Call et al.

(10) Patent No.: US 9,131,939 B1
(45) Date of Patent: Sep. 15, 2015

(54) DEVICE FOR PERCUTANEOUSLY DELIVERING A CARDIAC IMPLANT THROUGH THE APPLICATION OF DIRECT ACTUATION FORCES EXTERNAL TO THE BODY

(75) Inventors: Aaron M. Call, Mesa, AZ (US); Edward I. McNamara, Chelmsford, MA (US); Christopher C. Lee, Tewksbury, MA (US); Dennis M. Goodine, Dracut, MA (US); Megan E. Holmes, Nashua, NH (US)

(73) Assignee: MITRALIGN, INC., Tewksbury, MA (US)

( * ) Notice: Subject to any disclaimer, the term of this patent is extended or adjusted under 35 U.S.C. 154(b) by 888 days.

(21) Appl. No.: 12/394,528

(22) Filed: Feb. 27, 2009

Related U.S. Application Data

(60) Provisional application No. 61/031,798, filed on Feb. 27, 2008.

(51) Int. Cl.
*A61B 17/04* (2006.01)

(52) U.S. Cl.
CPC ......... *A61B 17/0487* (2013.01); *A61B 17/0401* (2013.01); *A61B 2017/0409* (2013.01); *A61B 2017/0414* (2013.01); *A61B 2017/0488* (2013.01)

(58) Field of Classification Search
USPC .................. 606/232; 24/325, 115 I, 115 L
See application file for complete search history.

(56) References Cited

U.S. PATENT DOCUMENTS

| 1,518,523 | A | | 12/1924 | Kubik | |
|---|---|---|---|---|---|
| 2,245,030 | A | * | 6/1941 | Gottesfeld et al. | 251/7 |
| 2,595,511 | A | * | 5/1952 | Butler | 251/6 |
| 2,866,340 | A | * | 12/1958 | Goldberg | 73/864.11 |
| 3,135,259 | A | | 6/1964 | Evans | |
| 3,215,395 | A | * | 11/1965 | Nettie Gorbar | 251/6 |
| 3,572,804 | A | * | 3/1971 | Nims et al. | 24/115 L |
| 3,628,221 | A | | 12/1971 | Pasbrig | |
| 3,685,787 | A | * | 8/1972 | Adelberg | 251/6 |
| 3,766,610 | A | | 10/1973 | Thorsbakken | |
| 3,900,184 | A | * | 8/1975 | Burke et al. | 251/6 |
| 3,952,377 | A | | 4/1976 | Morell | |
| 3,960,149 | A | * | 6/1976 | Bujan | 604/250 |
| 3,984,081 | A | * | 10/1976 | Hoganson | 251/6 |
| 4,065,093 | A | * | 12/1977 | Phillips | 251/6 |
| 4,148,224 | A | | 4/1979 | Craig | |
| 4,406,440 | A | * | 9/1983 | Kulle et al. | 251/6 |
| 4,455,717 | A | | 6/1984 | Gray | |
| 4,719,671 | A | | 1/1988 | Ito et al. | |
| 4,727,628 | A | | 3/1988 | Rudholm | |
| 4,750,492 | A | * | 6/1988 | Jacobs | 606/230 |

(Continued)

*Primary Examiner* — Dianne Dornbusch
*Assistant Examiner* — Robert Lynch
(74) *Attorney, Agent, or Firm* — Leason Ellis LLP

(57) ABSTRACT

A locker for securing one or more tensioning members and a method of using the same is described. The locker includes a locker body having a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. A hub surrounds the locker body such that the locker body is retractable with respect to the hub. Retraction of the locker body causes the movable member to move distally from the first position to the second position.

16 Claims, 13 Drawing Sheets

(56) References Cited

U.S. PATENT DOCUMENTS

| | | | |
|---|---|---|---|
| 5,078,731 A | 1/1992 | Hayhurst | |
| 5,123,914 A | 6/1992 | Cope | |
| 5,137,517 A * | 8/1992 | Loney et al. | 604/159 |
| 5,258,015 A | 11/1993 | Li et al. | |
| 5,356,412 A | 10/1994 | Golds et al. | |
| 5,366,458 A | 11/1994 | Korthoff et al. | |
| 5,368,599 A | 11/1994 | Hirsch et al. | |
| 5,369,849 A | 12/1994 | De France | |
| 5,372,146 A | 12/1994 | Branch | |
| 5,383,905 A | 1/1995 | Golds et al. | |
| 5,391,173 A | 2/1995 | Wilk | |
| 5,403,331 A | 4/1995 | Chesterfield et al. | |
| 5,413,585 A | 5/1995 | Pagedas | |
| 5,464,427 A | 11/1995 | Curtis et al. | |
| 5,486,197 A | 1/1996 | Le et al. | |
| 5,562,689 A | 10/1996 | Green et al. | |
| 5,584,835 A * | 12/1996 | Greenfield | 606/232 |
| 5,584,861 A | 12/1996 | Swain et al. | |
| 5,626,590 A | 5/1997 | Wilk | |
| 5,630,824 A | 5/1997 | Hart | |
| 5,643,295 A | 7/1997 | Yoon | |
| 5,669,935 A | 9/1997 | Rosenman et al. | |
| 5,681,351 A | 10/1997 | Jamiolkowski et al. | |
| 5,695,505 A | 12/1997 | Yoon | |
| 5,702,397 A * | 12/1997 | Goble et al. | 606/232 |
| 5,725,539 A | 3/1998 | Matern | |
| 5,725,556 A | 3/1998 | Moser et al. | |
| 5,735,877 A | 4/1998 | Pagedas | |
| 5,741,301 A | 4/1998 | Pagedas | |
| 5,810,851 A | 9/1998 | Yoon | |
| 5,814,051 A * | 9/1998 | Wenstrom, Jr. | 606/104 |
| 5,849,019 A | 12/1998 | Yoon | |
| 5,861,004 A | 1/1999 | Kensey et al. | |
| 5,895,391 A * | 4/1999 | Farnholtz | 606/108 |
| 5,895,393 A | 4/1999 | Pagedas | |
| 5,899,921 A | 5/1999 | Caspari et al. | |
| 5,902,321 A | 5/1999 | Caspari et al. | |
| 5,957,953 A * | 9/1999 | DiPoto et al. | 606/232 |
| 5,964,769 A | 10/1999 | Wagner et al. | |
| 5,972,001 A | 10/1999 | Yoon | |
| 6,010,525 A | 1/2000 | Bonutti et al. | |
| 6,015,428 A | 1/2000 | Pagedas | |
| 6,066,160 A | 5/2000 | Colvin et al. | |
| 6,086,608 A | 7/2000 | Ek et al. | |
| 6,099,553 A | 8/2000 | Hart et al. | |
| 6,126,677 A | 10/2000 | Ganaja et al. | |
| 6,159,234 A | 12/2000 | Bonutti et al. | |
| 6,200,329 B1 | 3/2001 | Fung et al. | |
| 6,231,592 B1 | 5/2001 | Bonutti et al. | |
| 6,290,711 B1 | 9/2001 | Caspari et al. | |
| 6,293,961 B2 | 9/2001 | Schwartz et al. | |
| 6,306,159 B1 | 10/2001 | Schwartz et al. | |
| 6,319,269 B1 | 11/2001 | Li | |
| 6,319,271 B1 | 11/2001 | Schwartz et al. | |
| 6,368,343 B1 | 4/2002 | Bonutti et al. | |
| 6,391,030 B1 | 5/2002 | Wagner et al. | |
| 6,409,743 B1 | 6/2002 | Fenton, Jr. | |
| 6,423,088 B1 | 7/2002 | Fenton, Jr. | |
| 6,432,123 B2 | 8/2002 | Schwartz et al. | |
| 6,468,293 B2 | 10/2002 | Bonutti et al. | |
| 6,475,230 B1 | 11/2002 | Bonutti et al. | |
| 6,517,556 B1 | 2/2003 | Monassevitch | |
| 6,524,328 B2 | 2/2003 | Levinson | |
| 6,527,794 B1 | 3/2003 | McDevitt et al. | |
| 6,569,187 B1 | 5/2003 | Bonutti et al. | |
| 6,575,987 B2 | 6/2003 | Gellman et al. | |
| 6,585,750 B2 | 7/2003 | Bonutti et al. | |
| 6,599,311 B1 | 7/2003 | Biggs et al. | |
| 6,660,023 B2 | 12/2003 | McDevitt et al. | |
| 6,682,533 B1 | 1/2004 | Dinsdale et al. | |
| 6,770,076 B2 * | 8/2004 | Foerster | 606/326 |
| 6,814,742 B2 | 11/2004 | Kimura et al. | |
| 6,855,157 B2 | 2/2005 | Foerster et al. | |
| 6,932,835 B2 | 8/2005 | Bonutti et al. | |
| 6,972,027 B2 | 12/2005 | Fallin et al. | |
| 6,986,775 B2 | 1/2006 | Morales et al. | |
| 6,997,189 B2 | 2/2006 | Biggs et al. | |
| 7,033,379 B2 | 4/2006 | Peterson | |
| 7,033,380 B2 | 4/2006 | Schwartz et al. | |
| 7,048,755 B2 | 5/2006 | Bonutti et al. | |
| 7,081,126 B2 | 7/2006 | McDevitt et al. | |
| 7,083,638 B2 * | 8/2006 | Foerster | 606/232 |
| 7,094,240 B2 | 8/2006 | Molz, IV et al. | |
| 7,094,251 B2 | 8/2006 | Bonutti et al. | |
| 7,101,395 B2 | 9/2006 | Tremulis et al. | |
| 7,144,415 B2 * | 12/2006 | Del Rio et al. | 606/232 |
| 7,147,652 B2 | 12/2006 | Bonutti et al. | |
| 7,517,357 B2 * | 4/2009 | Abrams et al. | 606/232 |
| 7,875,056 B2 * | 1/2011 | Jervis et al. | 606/232 |
| 2002/0111653 A1 * | 8/2002 | Foerster | 606/232 |
| 2003/0167062 A1 | 9/2003 | Gambale et al. | |
| 2003/0195562 A1 | 10/2003 | Collier et al. | |
| 2003/0195563 A1 | 10/2003 | Foerster | |
| 2003/0229377 A1 | 12/2003 | Tong | |
| 2004/0024420 A1 | 2/2004 | Lubbers et al. | |
| 2004/0098050 A1 | 5/2004 | Foerster et al. | |
| 2004/0133239 A1 | 7/2004 | Singhatat | |
| 2004/0147958 A1 | 7/2004 | Lam et al. | |
| 2004/0153103 A1 | 8/2004 | Schwartz et al. | |
| 2004/0162568 A1 | 8/2004 | Saadat et al. | |
| 2004/0193191 A1 | 9/2004 | Starksen et al. | |
| 2004/0220616 A1 | 11/2004 | Bonutti et al. | |
| 2004/0225183 A1 | 11/2004 | Michlitsch et al. | |
| 2004/0225305 A1 | 11/2004 | Ewers et al. | |
| 2004/0230223 A1 | 11/2004 | Bonutti et al. | |
| 2004/0236374 A1 | 11/2004 | Bonutti et al. | |
| 2004/0243227 A1 | 12/2004 | Starksen et al. | |
| 2004/0260344 A1 | 12/2004 | Lyons et al. | |
| 2005/0004602 A1 | 1/2005 | Hart et al. | |
| 2005/0033319 A1 | 2/2005 | Gambale et al. | |
| 2005/0055052 A1 | 3/2005 | Lombardo et al. | |
| 2005/0055087 A1 | 3/2005 | Starksen | |
| 2005/0059985 A1 | 3/2005 | Kimura | |
| 2005/0075653 A1 | 4/2005 | Saadat et al. | |
| 2005/0085855 A1 | 4/2005 | Forsberg | |
| 2005/0096699 A1 | 5/2005 | Wixey et al. | |
| 2005/0119675 A1 | 6/2005 | Adams et al. | |
| 2005/0149122 A1 | 7/2005 | McDevitt et al. | |
| 2005/0216059 A1 | 9/2005 | Bonutti et al. | |
| 2005/0222488 A1 | 10/2005 | Chang et al. | |
| 2005/0222489 A1 | 10/2005 | Rahdert et al. | |
| 2005/0228422 A1 | 10/2005 | Machold et al. | |
| 2005/0245945 A1 | 11/2005 | Ewers et al. | |
| 2005/0251157 A1 | 11/2005 | Saadat et al. | |
| 2005/0251202 A1 | 11/2005 | Ewers et al. | |
| 2005/0251205 A1 | 11/2005 | Ewers et al. | |
| 2005/0251206 A1 | 11/2005 | Maahs et al. | |
| 2005/0251207 A1 | 11/2005 | Flores et al. | |
| 2005/0251208 A1 | 11/2005 | Elmer et al. | |
| 2005/0251209 A1 | 11/2005 | Saadat et al. | |
| 2005/0251210 A1 | 11/2005 | Westra et al. | |
| 2005/0267534 A1 | 12/2005 | Bonutti et al. | |
| 2005/0277986 A1 | 12/2005 | Foerster et al. | |
| 2005/0288709 A1 | 12/2005 | Fallin et al. | |
| 2005/0288710 A1 | 12/2005 | Fallin et al. | |
| 2005/0288711 A1 | 12/2005 | Fallin et al. | |
| 2006/0004409 A1 | 1/2006 | Nobis et al. | |
| 2006/0004410 A1 | 1/2006 | Nobis et al. | |
| 2006/0058844 A1 | 3/2006 | White et al. | |
| 2006/0106422 A1 * | 5/2006 | Del Rio et al. | 606/232 |
| 2006/0122633 A1 | 6/2006 | To et al. | |
| 2007/0276437 A1 * | 11/2007 | Call et al. | 606/232 |
| 2008/0228165 A1 | 9/2008 | Spence et al. | |
| 2012/0109155 A1 | 5/2012 | Robinson et al. | |

* cited by examiner

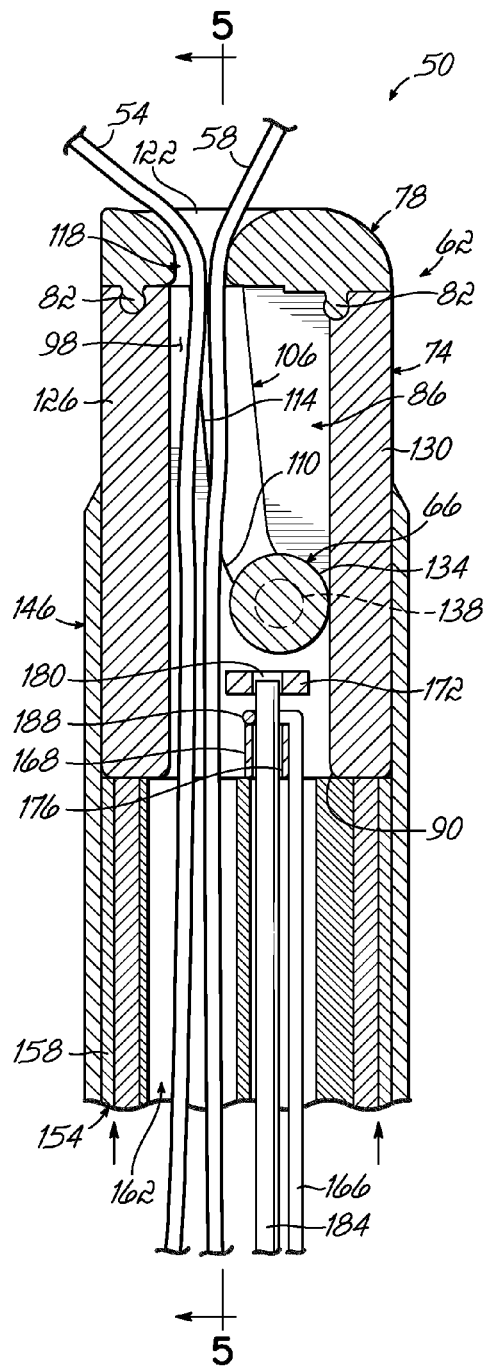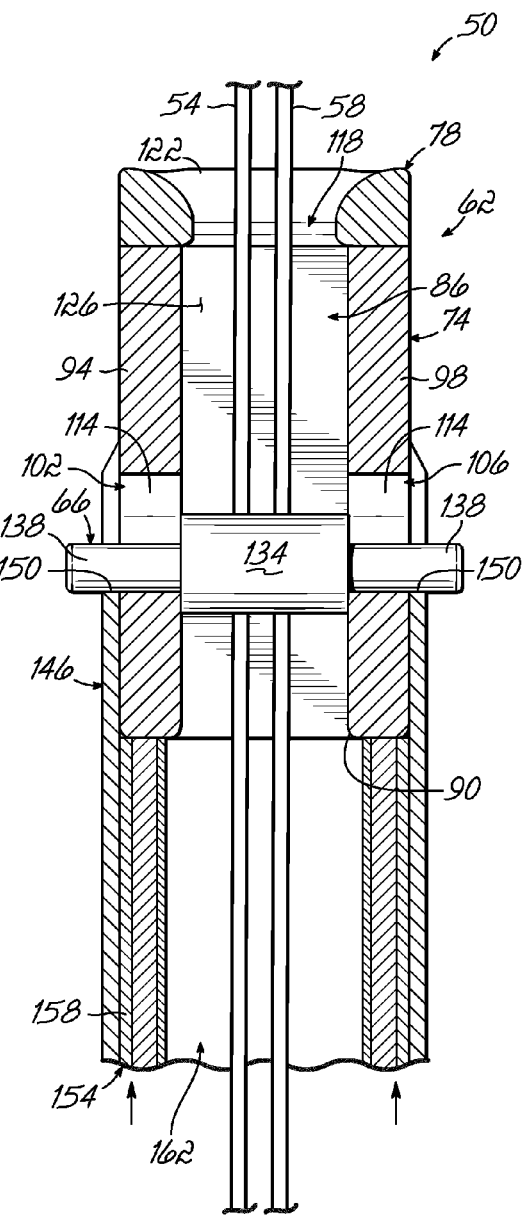
FIG. 4
FIG. 5

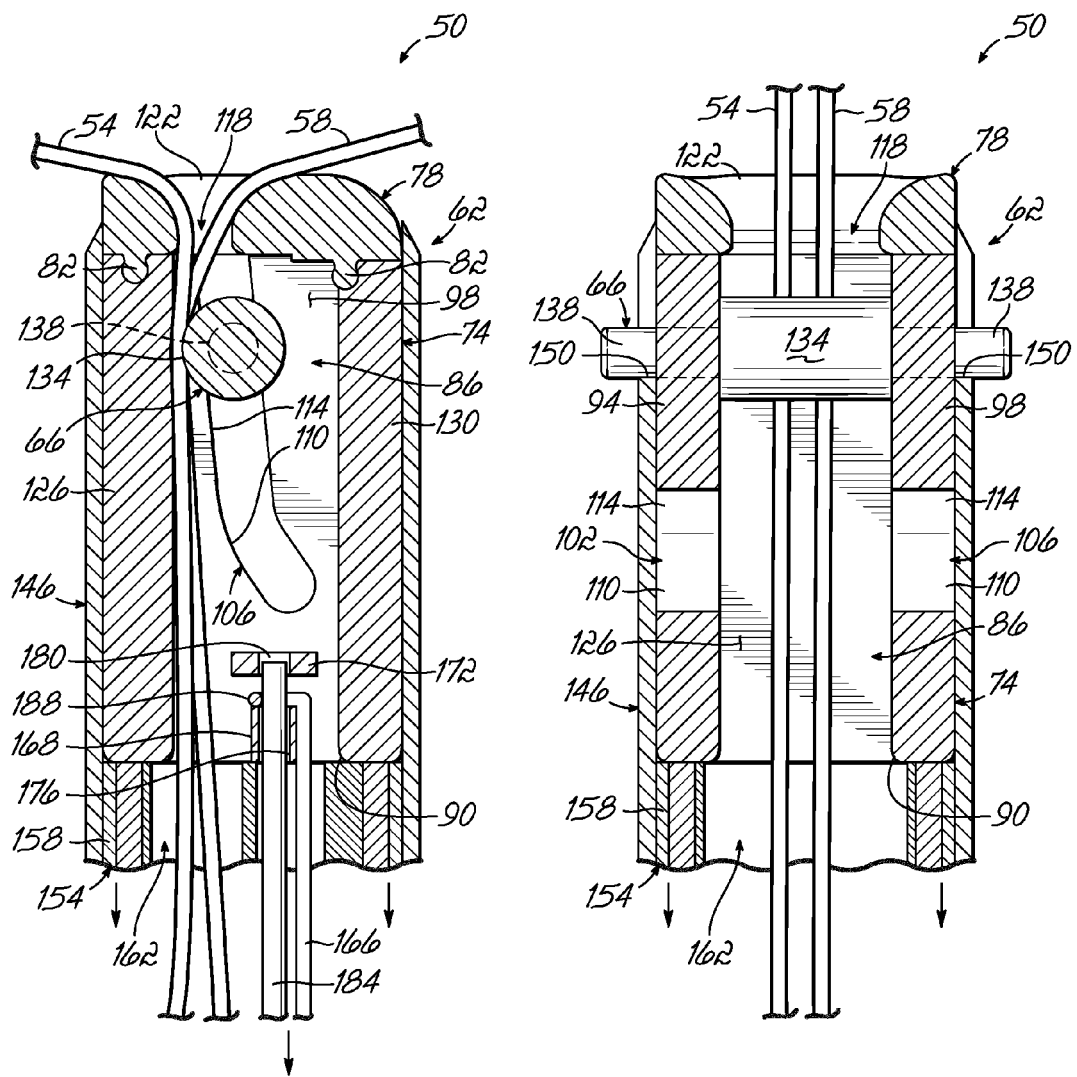

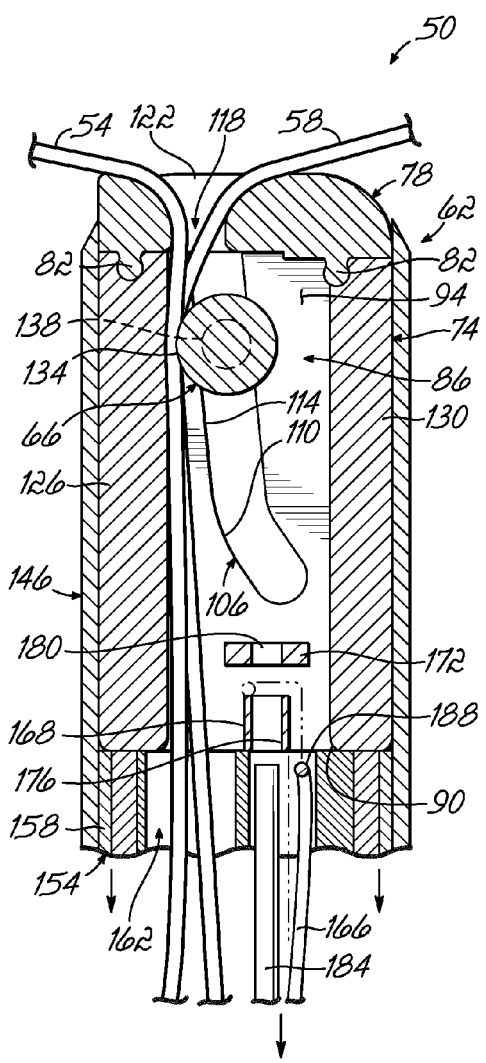
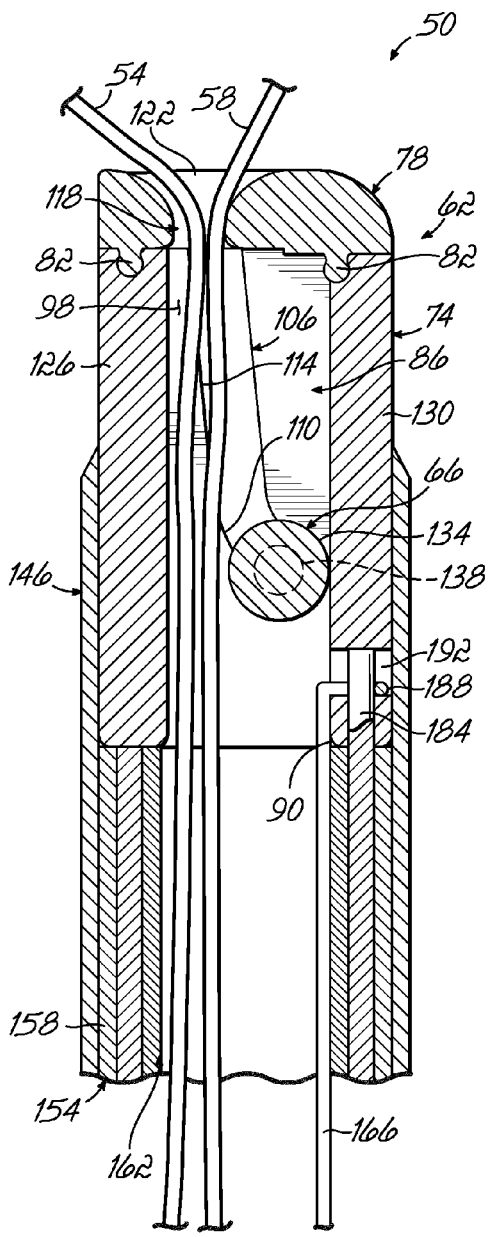
FIG. 8
FIG. 9

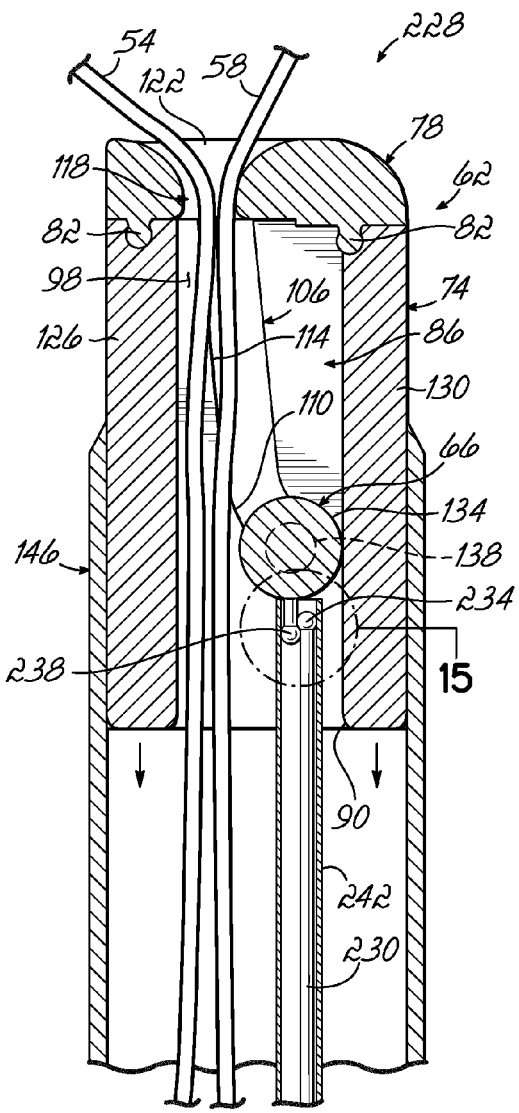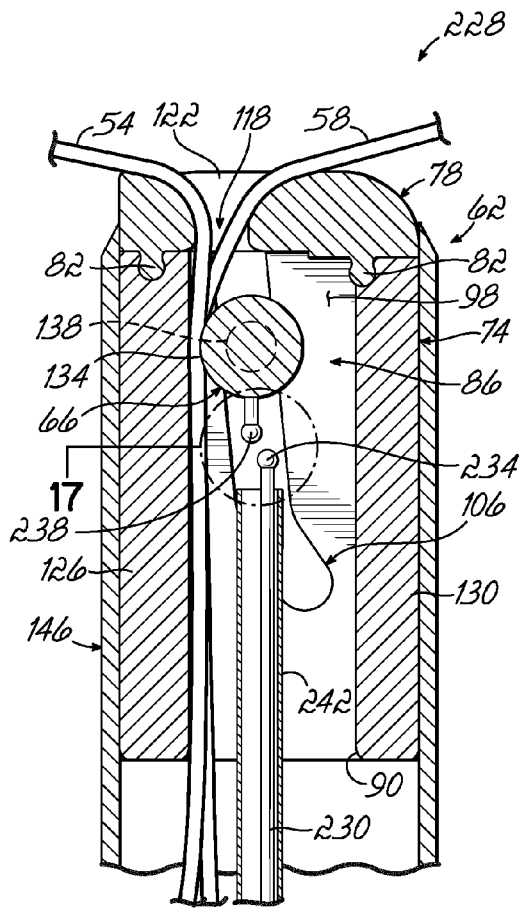
FIG. 14  FIG. 16
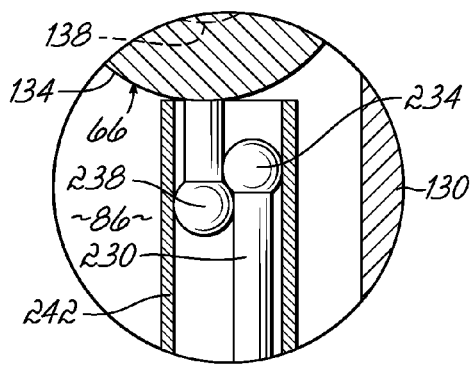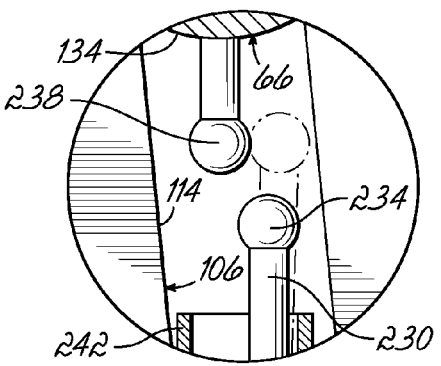
FIG. 15  FIG. 17

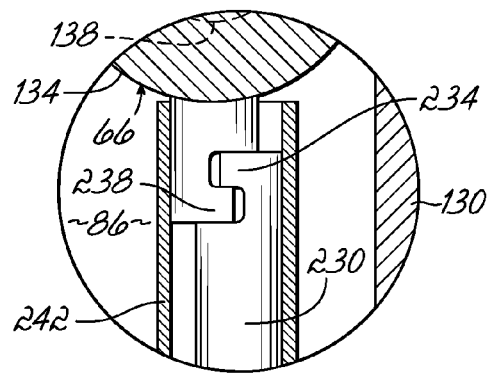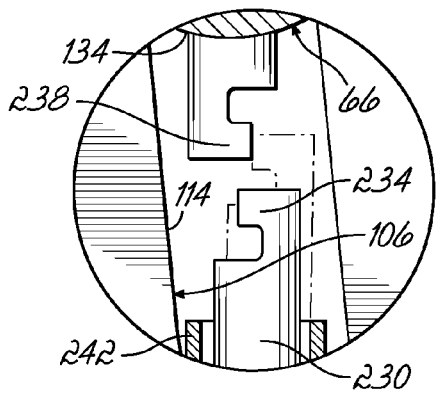
FIG. 18      FIG. 19
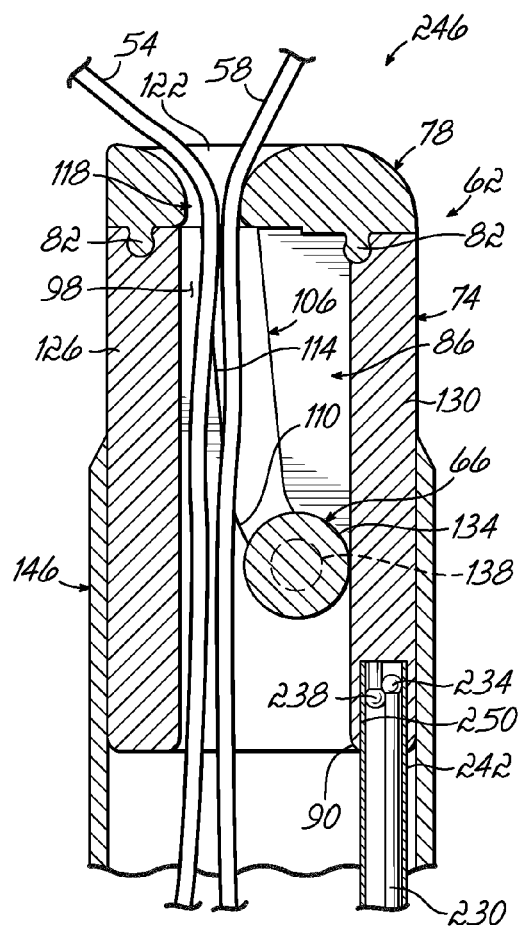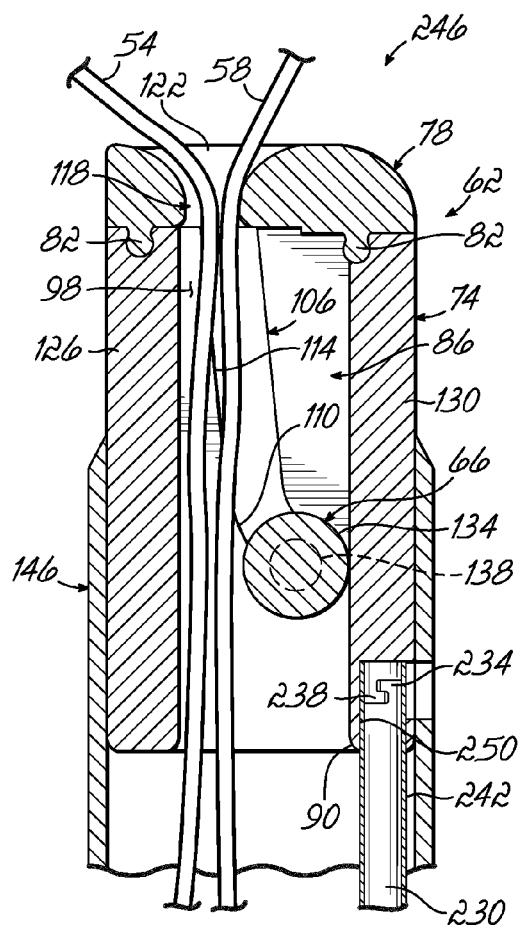
FIG. 20      FIG. 21

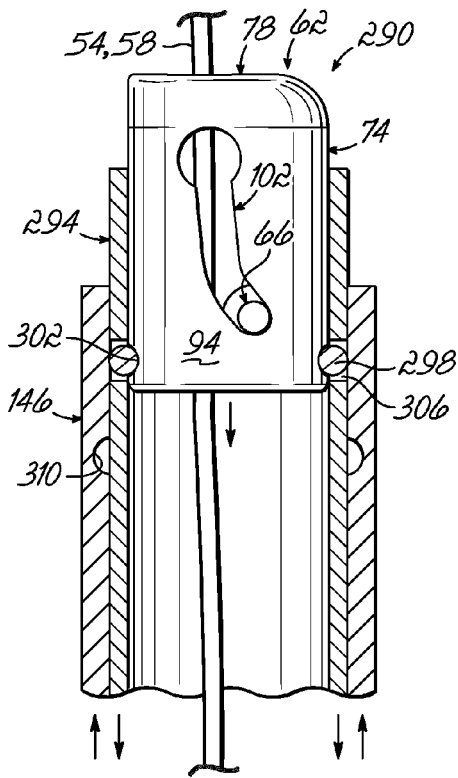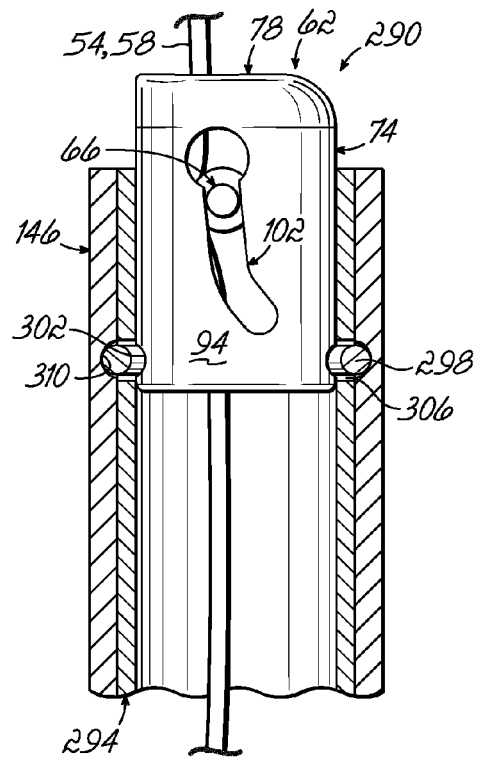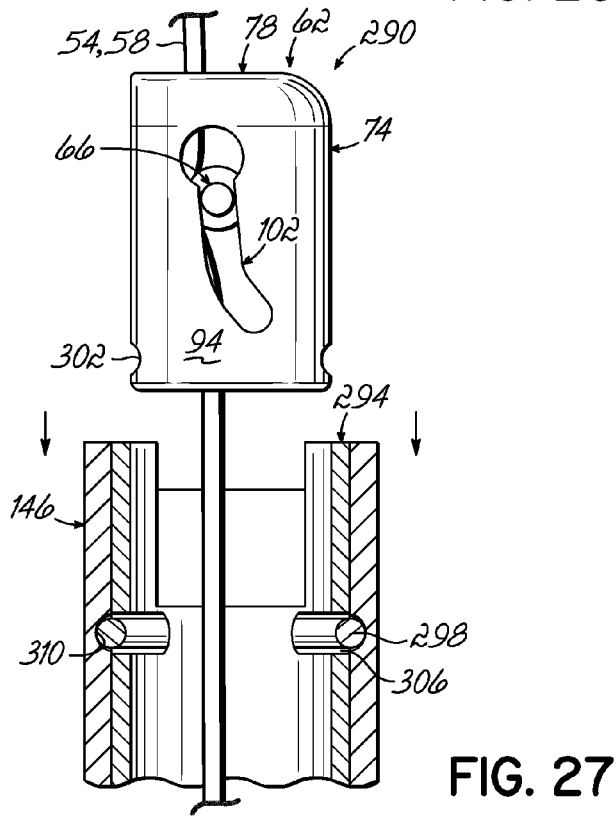
FIG. 25
FIG. 26
FIG. 27

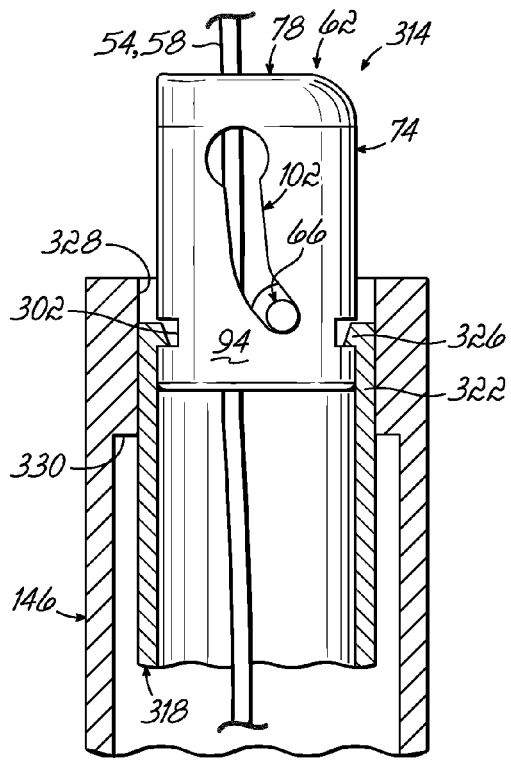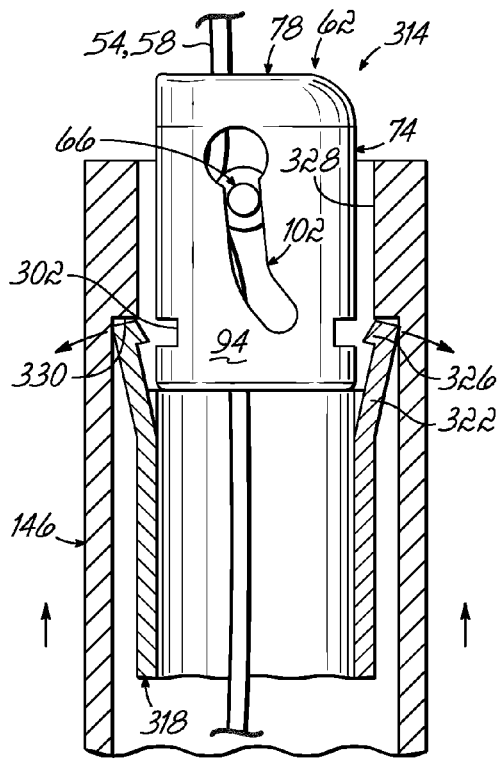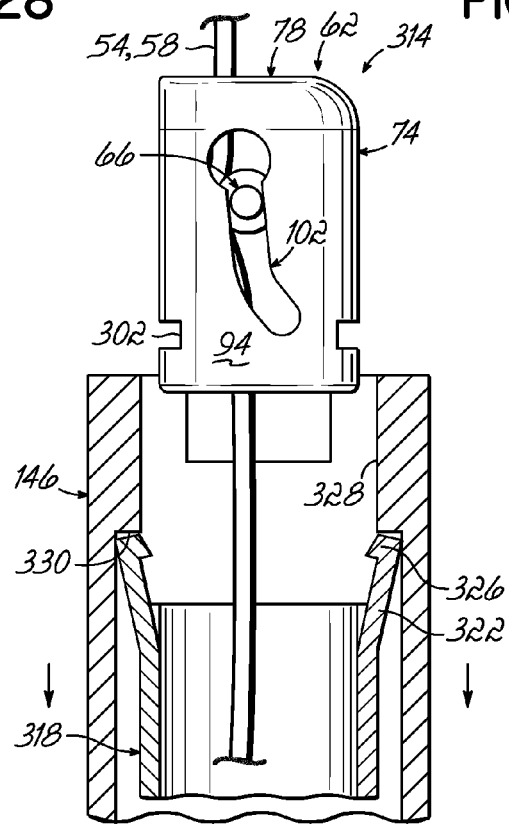

DEVICE FOR PERCUTANEOUSLY DELIVERING A CARDIAC IMPLANT THROUGH THE APPLICATION OF DIRECT ACTUATION FORCES EXTERNAL TO THE BODY

This application claims the priority of U.S. Provisional Patent Application Ser. No. 61/031,798, filed on Feb. 27, 2008, the disclosure of which is incorporated by reference herein. This application is also related to U.S. application Ser. No. 11/753,921, filed on May 25, 2007, the disclosure of which is also incorporated by reference herein.

TECHNICAL FIELD

The present invention generally relates to lockers for use during catheter-based surgical procedures and, more particularly, to lockers and methods of using such lockers to secure one or more tensioning members, such as sutures, extending from corresponding attachment points to a biological tissue, such as during the performance of an annuloplasty procedure.

BACKGROUND

Catheter-based surgical procedures may be employed to repair tissue, such as a defective mitral valve. One such catheter-based surgical procedure, commonly referred to as an annuloplasty, reduces the length of a posterior mitral valve leaflet through one or more plications. To that end, anchors are secured at a plurality of locations distributed about the annulus near the posterior leaflet of the mitral valve. Each anchor has a suture coupled thereto. The sutures are collectively gathered and pulled tight. As the sutures are pulled tight, the tissue between each pair of adjacent anchors is plicated, thereby shortening the length of the annulus and drawing the posterior leaflet toward the anterior leaflet to effect mitral valve repair.

During the surgical procedure, the sutures for each of the anchors extend to an incision site through the catheter. To preserve the plications, the sutures must be secured against movement. Because the procedures are catheter based, suture lockers are typically used because of the small diameter of the cannula or catheter.

There is generally a need for an improved locker to secure one or more tensioning members, such as sutures, against relative movement during and after a catheter-based surgical procedure.

SUMMARY

In one illustrative embodiment of the present invention, a locker for securing one or more tensioning members is described. The locker includes a locker body having a passageway through which the tensioning members extend. A movable member is coupled to the locker body and traverses the passageway. The movable member is movable between a first position within the passageway in which the one or more tensioning members are movable relative to the locker body and a second position within the passageway in which the one or more tensioning members are locked relative to the locker body. A hub surrounds the locker body such that the locker body is retractable with respect to the hub. Retraction of the locker body causes the movable member to move distally from the first position to the second position.

In another illustrative embodiment of the present invention, another locker for securing one or more tensioning members is described. The locker includes a locker body having a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. A hub surrounds the locker body such that the locker body is retractable with respect to the hub. A proximally-extending member extends from the locker body to an incision site into the body of the patient. The proximally-extending member is operable to retract the locker body with respect to the hub, which causes the movable member to move distally from the latent position to the activated position.

In yet another illustrative embodiment of the present invention, another locker is described. This embodiment of the locker includes a locker body having a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. The locker includes an actuating member having a proximal end portion and a distal end portion, where the distal end portion is proximate to the movable member. Pulling on the proximal end portion of the actuating member causes the distal end portion to move the movable member from the latent position to the activated position.

In another illustrative embodiment, the present invention is directed to a locker having a locker body with a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. The locker includes an actuating member having a distal inflation element. Inflating the distal inflation element causes the movable member to move from the latent position to the activated position.

Another illustrative embodiment includes a locker having a locker body with a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. The locker includes an elongated pin with an alignment key on a distal end of the elongated pin. The alignment key engages a matching alignment key that extends proximally from the movable member. Pushing distally on the elongated pin causes the movable member to move from the latent position to the activated position.

In another illustrative embodiment, a method of securing one or more tensioning members with one of the embodiments of the locker is described. The method includes directing the locker to the surgical site such that the tensioning members extend through the locker. A proximally-extending member is actuated, which causes the movable member to move distally. The actuating continues until the movable member is moved from the latent position to the activated position.

Another illustrative embodiment includes a method of securing one or more tensioning members with a locker having a locker body with a passageway through which the tensioning members extend. A movable member is coupled to the locker body and traverses the passageway. The movable member is movable between a first position within the passageway in which the one or more tensioning members are movable relative to the locker body and a second position within the passageway in which the one or more tensioning members are locked relative to the locker body. A hub surrounds the locker body such that the locker body is retractable with respect to the hub. The method of securing includes directing the locker to the surgical site and then retracting the locker body with respect to the hub. The retracting of the locker body causes the movable member to move distally from the first position to the second position.

In yet another illustrative embodiment, a method of securing one or more tensioning members with a locker is described. The locker includes a locker body having a passageway through which tensioning members extend. A movable member is coupled to the locker body and traverses the passageway. The movable member is movable between a latent position within the passageway in which the one or more tensioning members are movable relative to the locker body and an activated position within the passageway in which the one or more tensioning members are locked relative to the locker body. The locker includes an actuating member in contact with the movable member and extending proximally from the movable member. The method includes directing the locker to the surgical site and actuating the actuating member to cause the movable member to move from the latent position to the activated position.

Actuating the actuating member to move the movable member can include pushing the actuating member distally, proximally pulling on a proximal end of the actuating member, or inflating a distal inflation element of the actuating member.

BRIEF DESCRIPTION OF THE DRAWINGS

FIGS. 4-8 are cross-sectional views illustrating an exemplary method of using the suture locker shown in FIG. 1, which is shown with the tensioning members threaded through the suture locker.

FIG. 9 is a cross-sectional view illustrating an alternate embodiment, which is shown with the tensioning members threaded through the suture locker.

FIG. 14 is a cross-sectional view illustrating an alternate embodiment of the suture locker.

FIG. 15 is an enlarged cross-sectional view of the alternate embodiment illustrated in FIG. 14.

FIG. 16 is a cross-sectional view illustrating an exemplary method of using the alternate embodiment illustrated in FIG. 14.

FIG. 17 is an enlarged cross-sectional view of the alternate embodiment shown in FIG. 16.

FIGS. 18-19 are enlarged cross-sectional views of another alternative embodiment for the suture locker shown in FIGS. 14-17.

FIGS. 20-21 are cross-sectional views illustrating two additional embodiments of the suture locker.

FIGS. 25-27 are schematic views, in partial cross-section, of another illustrative embodiment of the present invention, including an exemplary method of using the same.

FIGS. 28-30 are schematic views, in partial cross-section, of yet another illustrative embodiment of the present invention, including an exemplary method of using the same.

DETAIL DESCRIPTION

Figure 1:
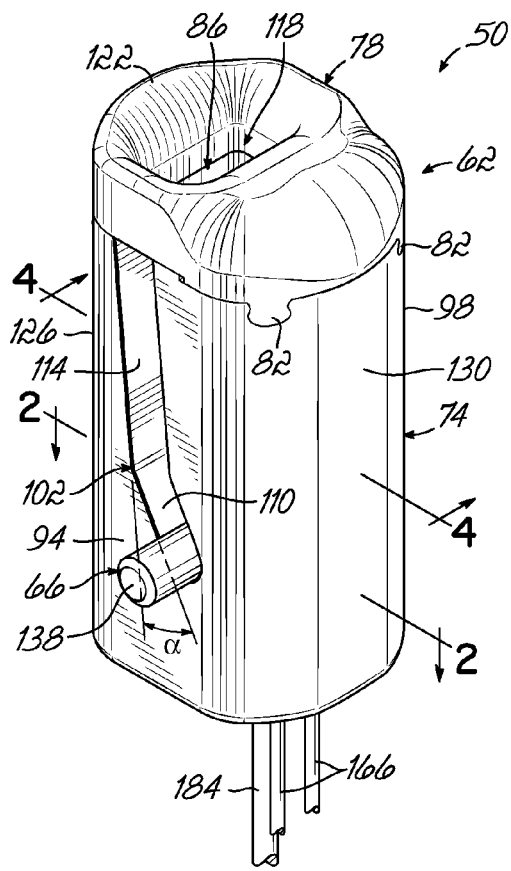
FIG. 1 is an elevational view of a suture locker constructed in accordance with one embodiment of the invention in which the suture locker is shown in the latent position.

With reference to FIG. 1, a suture locker 50 constructed in accordance with a first embodiment of the invention is utilized to selectively capture one or more tensioning members 54, 58 (FIG. 4) threaded through the suture locker 50. It will be readily appreciated that the tensioning members 54, 58 (FIG. 4) can take forms other than suture material, such as a cable or any other small diameter, flexible, semi-rigid or rigid material having a suitably high tensile strength for the intended use. Moreover, while the embodiments of the invention are referred to as suture lockers, the invention contemplates that the suture lockers can be used with tensioning members other than sutures.

The suture locker 50 has a first, latent position in which the tensioning members 54, 58 (FIG. 4) are movable with respect to the suture locker 50 and a second, activated position (shown below in FIG. 6) in which the tensioning members 54, 58 (FIG. 4) are captured or locked against movement with respect to the suture locker 50. The suture locker 50 can be used in conjunction with tensioning members 54, 58 (FIG. 4) extending from tissue anchors (not shown), such as those shown and described in commonly-owned U.S. application Ser. No. 11/174,951. Further, while embodiments of the invention generally refer to tensioning members 54, 58 (FIG. 4), it would be understood that the suture locker 50 is also operative with a single tensioning member, i.e. a single suture.

The suture locker 50 comprises an assembly that includes a locker body 62 and a movable member, such as a pin 66, for securing the tensioning members 54, 58 (FIG. 4). The locker body 62 includes a base member 74 and a contoured cap 78 closing an open end of the base member 74. The base member 74 and cap 78 constitute separate components of the assembly comprising the locker body 62 so that the pin 66 can be positioned within the locker body 62. Accordingly, the cap 78 can include multiple projections 82, spaced apart, to engage corresponding recesses defined in a confronting distal edge of the locker body 62. During a surgical procedure, the cap 78 is located at the distal end of the suture locker 50 and proximal to the surgical site within the body of a patient (not shown) from which the tensioning members 54, 58 (FIG. 4) extend.

Figure 2:
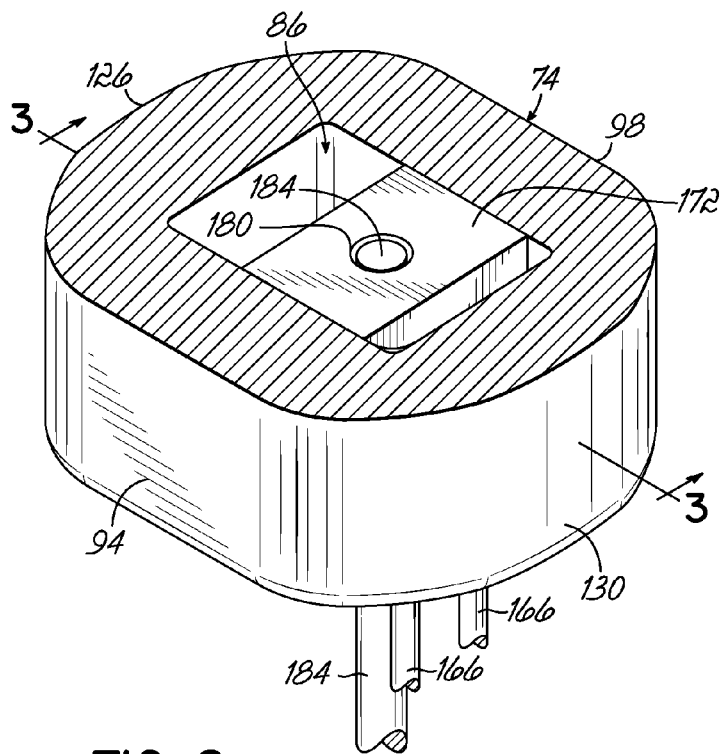
FIG. 2 is an elevational view of the suture locker shown in FIG. 1, taken along the line 2-2 in FIG. 1.
Figure 3:
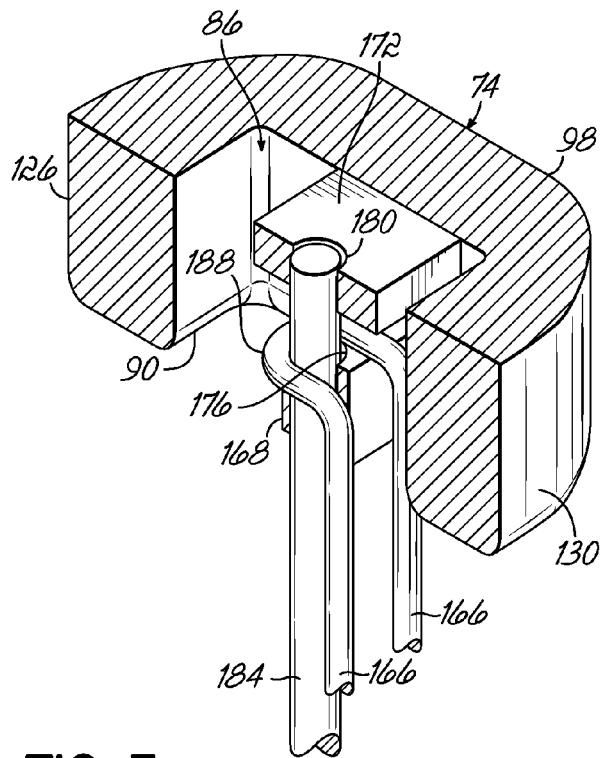
FIG. 3 is a cross-sectional view of the suture locker shown in FIG. 1, taken along the line 3-3 in FIG. 2.

The locker body 62, which may be tubular and open ended, bounds a cavity or passageway 86 (FIG. 2) that extends from a proximal first aperture 90 (FIG. 3) at a proximal end of the locker body 62 toward the distal end to which the cap 78 is attached. Opposite sidewalls 94, 98 of the base member 74 of the locker body 62 include slots 102, 106, respectively, that are generally oriented in a proximal-distal direction and that communicate with the passageway 86 (FIG. 2). Each slot 102, 106 includes a relatively short segment 110 near the proximal end of the locker body 62 and a relatively long segment 114 extending distally therefrom and intersecting the short segment 110 at a shallow acute angle, a (FIG. 1). The angle α is sufficient so that tensioning members 54, 58 (FIG. 4) are movable relative to the locker body 62 when the pin 66 is located in the short segment 110. The orientation of the long segment 114 is nearer to being parallel with the proximal-distal direction.

The cap 78 includes a passageway 118 that, when the suture locker 50 is assembled, permits access to the passageway 86 (FIG. 2) of the locker body 62 through a distal aperture 122. The passageway 118 of the cap 78 smoothly merges with the passageway 86 (FIG. 2) in the locker body 62. The tensioning members 54, 58 (FIG. 4) are threaded through the passageways 86, 118. As illustrated, the contoured portions of the cap 78 extending from a distal second aperture 122 toward the passageway 118 can be smoothly curved inwardly in a convergent manner so that the cross-sectional area, when viewed along the proximal-distal direction, of the passageway 118 can narrow in a distal to proximal direction. The cross-sectional area of the passageway 118 can be smaller than the corresponding cross-sectional area of passageway 86 (FIG. 2) within the locker body 62.

The passageway 118 of the cap 78 can be offset transversely or laterally from an axis of symmetry extending through the passageway 86 (FIG. 2). As a result, the passageway 118 can be positioned closer to a reverse wall 126 of the locker body 62 than front wall 130 while remaining approximately centered in position between sidewalls 94, 98. However, these illustrated structural dimensions should not be considered limiting.

The cap 78, when assembled with the base member 74, closes the distal end of the slot 102. This constrains the distal movement of the pin 66 relative to the locker body 62. Proximal movement of the pin 66 is constrained at the opposite end by the closed ends of the slots 102, 106. Accordingly, the pin 66 is constrained to move within the slot 102 along a path defined by the short and long segments 110, 114.

Though not specifically illustrated, the locker body can alternatively be constructed as a single component. The pin can then be inserted through an enlarged portion at a distal end of one of the slots.

The pin 66 can include a central section 134 (FIG. 5) and two end sections 138 extending distally from the central section 134 (FIG. 5). Each of the sections 138, 134, 138 are arranged along a longitudinal axis of the pin 66 and are cylindrical in cross-sectional area when viewed along the longitudinal axis. The end sections 138 have a diameter when viewed along the longitudinal axis that is smaller than a diameter of the central section 134 (FIG. 5).

Though it is not specifically shown, the pin 66 could further include caps located at the distal ends of each of the end sections 138. The caps can also have a cylindrical cross-sectional area when viewed along the longitudinal axis and can be generally larger in diameter than the diameter of the end sections 138.

The end sections 138 have a length along the longitudinal axis that is determined primarily by the wall thickness of the sidewalls 94, 98 of the locker body 62. The diameter, or largest dimension, of the end sections 138 is selected to be smaller than the width of the slot 102, 106 through the respective sidewalls 94, 98.

When the suture locker 50 is assembled and the pin 66 is engaged with the slots 102, 106 the exposed faces of the central section 134 (FIG. 5) bordering opposite and internal sides of the sidewalls 94, 98 act to limit the transverse movement of the pin 66 in a direction parallel to the longitudinal axis by contacting opposite confronting portions of the sidewalls 94, 98.

A hub 146 (FIG. 4) can surround the locker body 62. The hub 146 (FIG. 4) can be tubular and open ended, similar in shape to the base member 74. Some embodiments of the hub can include recesses 150 (FIG. 5) for receiving the end sections 138 of the pin 66, which extend laterally from the sidewalls 94, 98 of the base member 74. Though not shown, the hub can also be connected to a distal end catheter assembly that extends proximally to the incision site into the body of the patient.

The locker body 62 can be coupled to one embodiment of a catheter assembly 154 (FIG. 4), which is used to maneuver the suture locker 50 through the patient's vascular system to the surgical site as is generally known in the art. A catheter body 158 (FIG. 4) is constructed to include a passageway 162 (FIG. 4) that extends proximally from the proximal aperture 90 of the locker body 62 such that the tensioning members 54, 58 extend therethrough and without constraint.

As illustrated in FIGS. 1-9, the suture locker 50 can include a pull wire 166 for retracting the locker body 62 with respect to the hub 146. Additional structures for retracting the locker body 62 will also be described below. The pull wire 166 is constrained with the base member 74 by proximal and distal stationary plates 168, 172 shown in FIGS. 2 and 3. The proximal and distal plates 168, 172 can be molded from the same material as the base member 74 or separately constructed and attached to the base member 74 during its construction. The plates 168, 172 can traverse the passageway 86 just proximal to the slots 102, 106 so as to not interfere or constrain the movement of the pin 66 nor the tensioning members 54, 58 and to allow passage or movement of each relative to the pull wire 166. The proximal and distal plates 168, 172 can further include orifices 176, 180 through which a retaining pin 184 traverses.

The pull wire 166 can be constructed from suture-like material; however, the construction or materials should not be considered limiting and alternative embodiments will be described in detail below. As shown, the pull wire 166 enters the passageway 86 from the aperture 90, forms a distal loop 188 about the retaining pin 184 and between the proximal and distal plates 168, 172, and returns through the aperture 90. In this way, the retaining pin 184 constrains the removal of the pull wire 166 from the locker body 62.

In use and with reference to FIGS. 1 and 4-7, during the catheter-based surgical procedure, the suture locker 50, and hub 146 are directed through the vascular network to the surgical site. The tensioning members 54, 58 can be threaded through the passageways 118, 86, 162 and are normally free to move with negligible resistance from the pin 66 as depicted in FIG. 4. The pin 66 of the suture locker 50 is held initially in a latent position, i.e. the short segment 110. The suture locker 50 is then pushed through the vascular network by the physician using a distally directed force applied to the catheter body 158. The catheter assembly 154 delivers the suture locker 50 to the surgical site, which can be confirmed by the in vivo visualization of a fluoroscopic marker on the suture locker 50 or a radio-opaque material used in constructing the base member 74.

As shown in FIG. 5, the end sections 138 of the pin 66 reside within the recesses 150 of the hub 146.

Once the suture locker 50 has been properly positioned at the surgical site, the pin 66 can then be moved into the activated position. To achieve this activated position, the physician applies a proximally-directed force to the pull wire 166 while the relative position of the hub 146 is maintained. The proximally-directed force retracts the locker body 62 with respect to the hub 146. The end sections 138 of the pin 66 are captured within the recesses 150 of the hub 146, which prevents the relative movement of the pin 66 with the locker body 62. As the proximally-directed force continues, the relative movements between the locker body 62 and the pin 66 effectively displaces the pin 66 in the distal direction toward the cap 78, following the contour of the slots 102, 106. Thus, the suture locker 50 moves from a latent position, shown in FIGS. 4 and 5, to an activated position, shown in FIGS. 6 and 7.

Once the pin 66 is within the long segment 114 of the slots 102, 106, i.e. the activated position, it pinches or compresses the tensioning members 54, 58 between the central section 134 of the pin 66 and a portion of the locker body 62 bordering the passageway 86. The pin 66 can be maintained in that position by frictional fit with the slots 102, 106. The physician can then cut the tensioning members 54, 58 to an appropriate length, e.g. proximal to the pin 66, or allow the tensioning members 54, 58 to remain extended through the suture locker 50 as shown in FIG. 8.

FIG. 8 also illustrates the finalizing of the catheter-based surgical procedure. That is, after the pin 66 has been moved into the activated position, the pull wire 166 can be removed. To remove the pull wire 166, the retaining pin 184 is first retracted from the locker body 62. This retraction allows the distal loop 188 of the pull wire 166 to be retracted from between the proximal and distal plates 168, 172 within the base member 74. After the retaining pin 184 and pull wire 166 are removed, the hub 146 and catheter assembly 154 can be retracted, leaving the suture locker 50 at the surgical site.

FIG. 9 illustrates an alternative location for the pull wire 166 and retaining pin 184 within the front wall 130 of the base member 74; however, the pull wire 166 could be positioned in any wall of the base member 74. This particular arrangement simplifies the construction of both the base member 74, by eliminating the proximal and distal plates 168, 172, and the catheter assembly 154 permitting for a single lumen catheter assembly 154. The distal loop 188 is formed within a window 192 around the retaining pin 184. In operation, the pull wire 166 and retaining pin 184 operate in a similar manner as was described previously in FIGS. 4-8.

Figure 10:
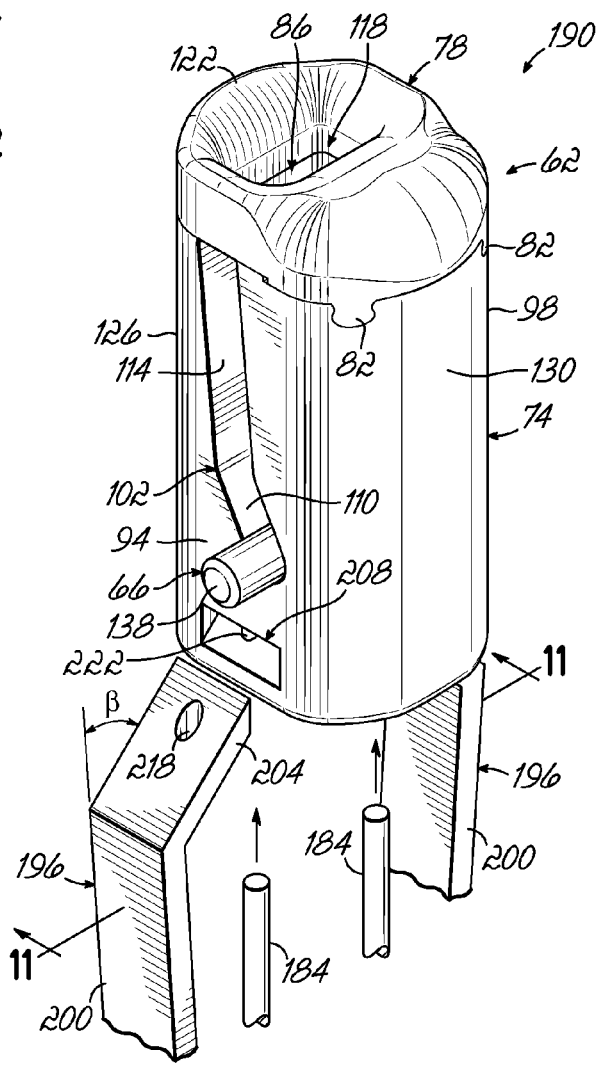
FIG. 10 is an elevational view of a suture locker constructed in accordance with another embodiment of the invention in which the suture locker is shown in the latent position

In another embodiment, the suture locker 190 includes at least one retraction member 196 extending proximally from the locker body 62, as shown in FIG. 10. The retraction member 196 can be constructed from a rigid, semi-rigid, or a flexible material. As illustrated, two retraction members 196 are used, each including an elongated portion 200 and an angled portion 204 extending distally from the elongated portion 200 and at an angle, β. The angled portion 204 projects into the locker body 62 through windows 208, 212 constructed within the sidewalls 94, 98 of the locker body 62 and proximal to the slots 102, 106. The windows 208, 212 are constructed with an angle that is substantially similar to the angle β such that the angled portion 204 of each retraction member 196 can be positioned into the window 208, 212 while the elongated portions 200 extend proximally and substantially parallel to the locker body 62. A slight convergence of the retraction members 196 is permitted so that the locker body 62 and retraction members 196 can be constrained within a catheter delivery system (not shown) or within the vascular network, generally.

The angled portions 204 of each retraction member 196 include a transverse opening 218 for receiving a retaining pin 184. The retaining pin 184 prevents the movement of the retraction members 196 from the locker body 62. The elongated portion 200 of each retraction member 196 extends proximally to outside the patient's body, allowing the physician to manipulate the suture locker 190, in vivo, at the surgical site. The retaining pins 184 each extend within peripheral passageways 222, 226 within the sidewalls 94, 98 of the locker body 62 and through the transverse openings 218 of each retraction member 196.

Figures 11, 12:
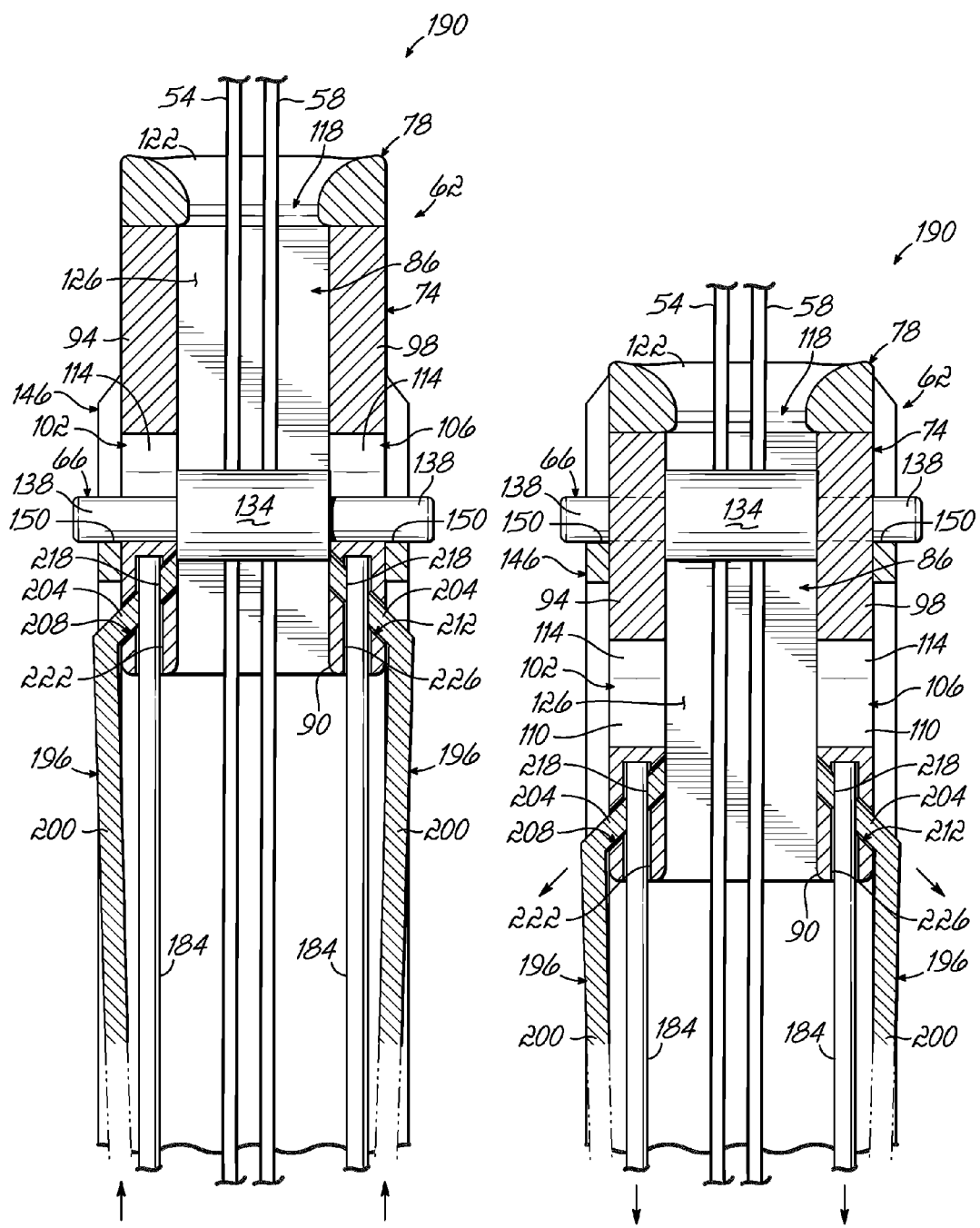
FIGS. 11-13 are cross-sectional views illustrating an exemplary method of using the suture locker shown in FIG. 10, which is shown with the tensioning members threaded through the suture locker.
Figure 13:
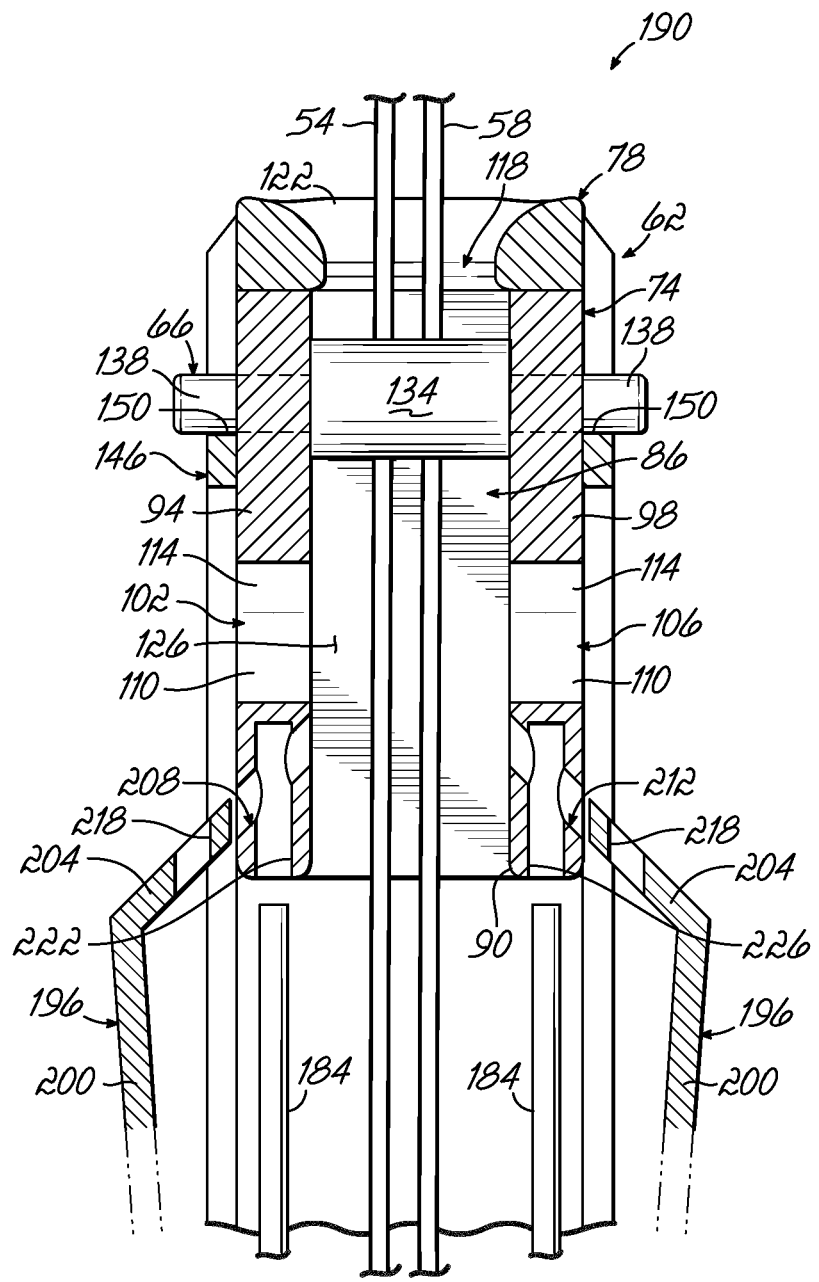

As was described above with respect to the previous embodiment, and as illustrated in FIGS. 11-13, the suture locker 190 with the hub 146 are directed to the surgical site. The tensioning members 54, 58 extend through the passageways 118, 86. Once the suture locker 190 is properly positioned, the physician pulls with a proximally-directed force on the retraction members 196 while the position of the hub 146 is maintained. The proximally-directed force retracts the suture locker 190 with respect to the hub 146 with the end sections 138 of the pin 66 being captured within the recesses 150 of the hub 146. As the proximally-directed force continues, the locker body 62 moves relative to the pin 66 within the slots 102, 106, as shown in FIG. 13.

Once the pin 66 is in the activated position, the retraction members 196 can be removed from the locker body 62 by first retracting the retaining pins 184. After the retaining pins 184 are removed, the retraction members 196 slide laterally out of the windows 208, 212. The physician can then cut the tensioning members 54, 58 to an appropriate length or allow the tensioning members 54, 58 to extend freely and proximally from the locker body 62.

Turning now to FIGS. 14-17 where yet another embodiment of a suture locker 228 is illustrated and includes an elongated pin 230 that extends proximally from the pin 66 and through the passageway 86 of the base member 74. The elongated pin 230 can be a rigid or semi-rigid rod construction, such as stainless steel, and includes an alignment key 234 on the distal end. The proximal end of the elongated pin 230 extends beyond the proximal aperture 90 and out of the body of the patient. In this way, the physician can remotely manipulate the position of the pin 66 from the latent to the activated position in a manner described below.

The alignment key 234 of the elongated pin 230 engages a matching alignment key 238 extending proximally from the pin 66. As shown in FIG. 14, the matching alignment key 238 can be interlocking balls; however, other shapes can be used and will be described below. When the pin 66 is in the latent position, the alignment key 234 of the elongated pin 230 engages the matching alignment key 238, which are positionally constrained within a narrow sheath 242. By constraining the alignment keys 234, 238 to within the narrow sheath 242, the suture locker 228 can be maintained in the latent position until it is properly positioned at the surgical site.

To place the suture locker 228 in the activated position, the physician applies a distally-directed force against the elongated pin 230 such that the alignment key 234 abuts the central section 134 of the pin 66 and causes the pin to move within the slots 102, 106 toward the cap 78. The pin 66 then follows the contour of the slots 102, 106 as it moves from a latent position, as shown in FIG. 14, to an activated position as shown in FIG. 16. As the pin 66 moves along the slots 102, 106, the alignment keys 234, 238 extend beyond the narrow sheath 242 and are free to move laterally with respect to one another. This greater freedom allows the interlocking balls to become disengaged, as shown in FIGS. 16 and 17, and allows the physician to retract the elongated pin 230 from the locker body 62.

Alternatively, the alignment keys 234, 238 can remain constrained within the narrow sheath 242 as the pin 66 is moved distally into the activated position. To disengage the alignment keys 234, 238, the physician can then retract the narrow sheath 242.

Other alignment key structures are envisioned, and can include, for example, interlocking steps shown in FIGS. 18 and 19.

FIGS. 20 and 21 illustrate an alternate location for the elongate pin 230 and the alignment keys 234, 238 within the suture locker 246. As shown, the elongated pin 230 is positioned within the front wall 130 of the base member 74; however, the elongated pin 230 could also be positioned in one of the sidewalls 94, 98 or the reverse wall 126. In use, the elongated pin 230 and alignment keys 234, 238 operate in a manner that is similar to the pull wire 166 (FIG. 1) or the retraction member 196 (FIG. 10). That is, the alignment keys 234, 238 are sufficiently constrained within a channel 250 and allow the locker body 62 to be retracted with respect to a hub 146.

In another embodiment, not specifically shown, the alignment keys 234, 238 can be constrained within a narrow sheath within the channel 250 while the locker body 62 is retracted relative to the hub 146. Retraction of the narrow sheath can then allow the alignment keys 234, 238 to disengage such that the elongate pin 230 can be retracted from the locker body. The alignment key 234, 238 can be engaged within the sheath 242, which can extend proximally from the locker 62.

Figure 22:
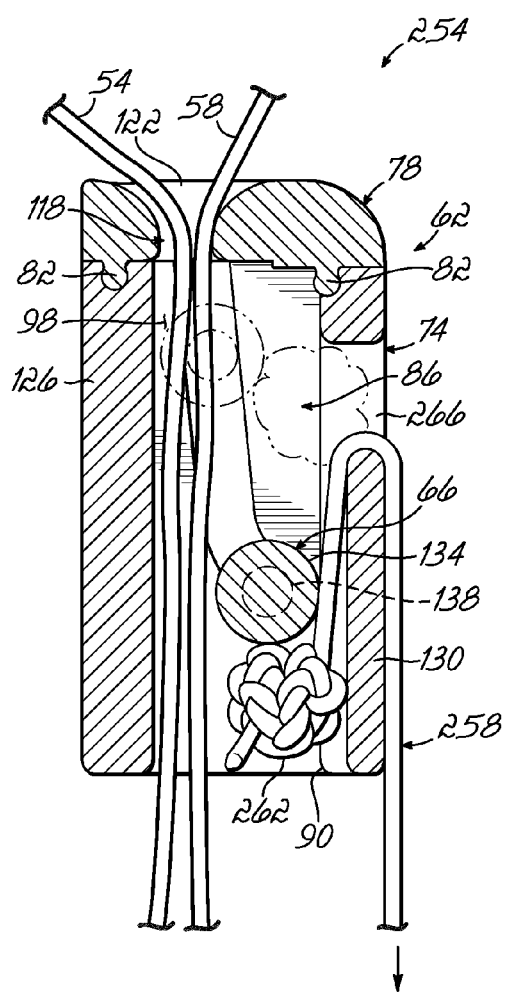
FIGS. 22-23 are cross-sectional views illustrating yet two additional embodiments of the suture locker with the latent position shown in solid and the activated position shown in phantom.
Figure 23:
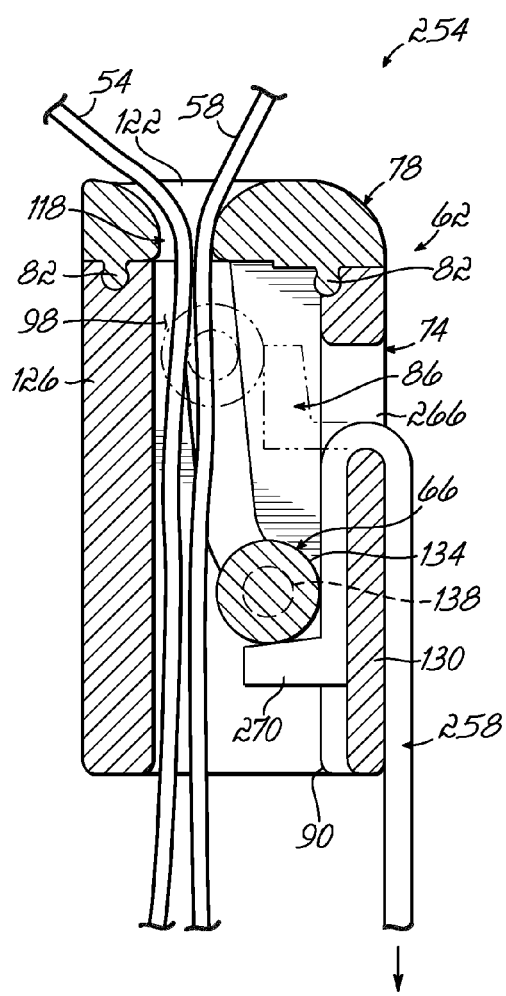
Figure 24:
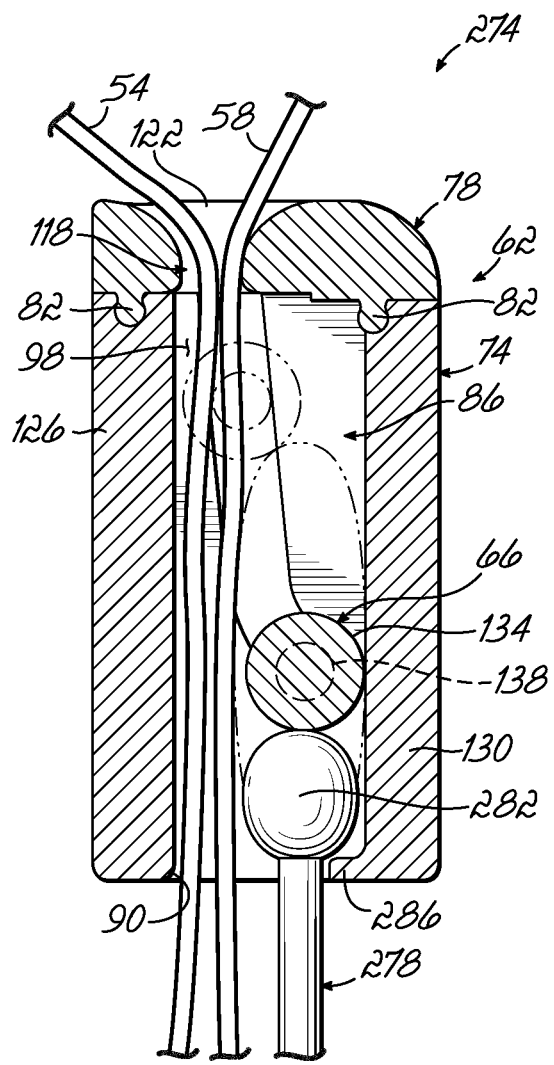
FIG. 24 is a cross-sectional view illustrating another embodiment of the suture locker with the latent position shown in solid and the activated position shown in phantom.

FIGS. 22-24 illustrate three additional embodiments for suture lockers with alternate methods of moving the pin 66 into the activated position.

The suture locker 254 of FIG. 22 includes an actuating member 258, which can be constructed from suture or wire material. The actuating member 258 includes a distal protrusion, illustrated here as a knot 262, on the distal end of the actuating member 258, which is located just proximal to the pin 66 in the latent position. The actuating member 258 extends distally from the pin 66 through a window 266 in the front wall 130 of the base member 74. The actuating member 258 traverses the window 266, laterally from the passageway 86, and extends proximally along the external surface of the front wall 130 to the incision site.

In use, the physician directs the suture locker 254 to the surgical site with the tensioning members 54, 58 extending therethrough. Once the suture locker 254 is properly positioned at the surgical site, the physician can pull on the proximal end of the actuating member 258 that extends proximally through the incision site. This proximally-directed force causes the knot 262 to move, initially, in a distal direction, thereby displacing the pin 66 within the slots 102, 106 from the latent to the activated position (shown in phantom). After the pin 66 is in the activated position, there is sufficient space between the proximal end of the pin 66 and the window 266 to allow the knot 262 to move laterally through the window 266 and disengage from the pin 66. The actuating member 258 is then retracted from the suture locker 254.

FIG. 23 illustrates an alternative construction of the actuating member 258 of FIG. 22. In FIG. 23, the actuating member 258 can be constructed from a more rigid material than the suture material shown in FIG. 22, and the distal protrusion includes a shim 270 extending laterally from a main axis of the actuating member 258. In use, the shim 270 operates in a manner similar to that described previously for the knot 262.

FIG. 24 illustrates another embodiment of a suture locker 274 that includes an actuating member 278 having a distal inflation element 282, such as a balloon, for displacing the pin 66 within the slots 102, 106 of the base member 74. Though not shown, the actuating member 278 can include an internal inflation channel in fluid communication with the distal inflation element 282. The base member 74 can include a proximal lip 286 that constrains the distal inflation element 282 within the base member 74 until it is fully deflated.

In use, once the suture locker 274 is appropriately positioned, the physician directs an inflation fluid through the inflation channel within the actuating member 278 and into the distal inflation element 282. As the interstitial pressure within the distal inflation element 282 increases, the distal inflation element 282 is inflated. The distal inflation element 282 can be constructed such that inflation mainly occurs in a longitudinal direction. Continued inflation, as shown in phantom, causes the distal inflation element 282 to contact the proximal end of the pin 66 and directs the pin 66 distally within the slots 102, 106 and into the activated position.

Turning now to FIGS. 25-27 where another embodiment of a suture locker 290 and a manner of using the same are shown. The suture locker 290, as shown in FIG. 25, includes a retraction member 294 that surrounds at least a distal portion of the exterior of the locker body 62 and extends proximally to the incision site. The retraction member 294 can be constructed from a rigid or semi-rigid material.

The retraction member 294 is maintained on the exterior of the locker body 62 by a retaining ring 298. The retaining ring 298 surrounds and engages the locker body 62 within a notch 302. In construction, the retaining ring 298 can be biased outwardly and is made from stainless steel, nitinol, or similar materials.

In preparing the suture locker 290 for the surgical procedure, the retaining ring 302 is positioned within a groove 306 within the retraction member 294, which are then aligned with the notch 302 within the locker body 62. The relative positions of the retraction member 294 to the locker body 62 are maintained by back-loading the retraction member 294, locker body 62, and retaining ring 302 into the hub 146. The inner surface of the hub 146 constrains the retaining ring to within the groove 306 and the notch 302.

In use, after the suture locker 290 is positioned at the surgical site, the physician pulls proximally on the retraction member 294 such that the locker body 62 is retracted relative to the hub 146 in a manner that is similar to previously described embodiments. During this pulling, the pin 66 is effectively moved distally from the latent position to the activated position, shown in FIG. 26. Additionally, after sufficient retraction of the locker body 62 with respect to the hub 146, the retaining ring 302 can align with a groove 310 on the inner surface of the hub 146. Once the retaining ring 302 is so aligned, the outwardly bias of the retaining ring 302 causes the retaining ring 302 to move into the groove 310 and eliminates the constraint between the retraction member 294 and the notch 302 in the locker body 62. Accordingly, the retraction member 294 and the hub 146 can be retracted from the locker body 62, as shown in FIG. 27.

Finally, FIGS. 28-30 illustrate yet another embodiment of a suture locker 314 and a manner of using the same. Similar to the suture locker 290 (FIG. 25), suture locker 314 includes a retraction member 318 that surrounds at least a proximal portion of the exterior of the locker body 62 and extends proximally to the incision site. The retraction member 318 further includes a distal biasing portion 322 that is biased outwardly. The distal biasing portion 322 includes an inwardly-directed protrusion 326 that can be inserted into the notch 302 of the locker body 62. The retraction member 318 can be constructed of stainless steel, nitinol, or other similar materials.

Alternatively, the distal biasing portion 322 can be constructed as a separate tip that is then welded, glued, or otherwise affixed to a catheter-like structure that extends proximally to the incision site.

In preparing the suture locker 314 for a catheter-based surgical procedure, the protrusion 326 of the distal biasing portion 322 is aligned with the notches 302 of the locker body 62. The retraction member 318 and the locker body 62 are then back-loaded into a distal constraining portion 328 of the hub 146. The distal constraining portion 328 maintains the protrusion 326 in contact with the notches 302 of the locker body 62.

The suture locker 314 is used in a manner that is similar to the embodiment shown in FIGS. 25-27. As shown in FIG. 29, after positioning the suture locker 314 at the surgical site, the surgeon pulls proximally on the retraction member 318 such that the pin 66 moves from the latent position to the activated position. During the retraction, the distal biasing portion 322 is retracted beyond the distal constraining portion 328 and to a back cut 330, which removes the constraint on the distal constraining portion 328 such that it is biased outward. Accordingly, the protrusion 326 is released from the notch 302 in the locker body 62. The hub 146 and the retraction member 318 can then be retracted from the suture locker 314, as shown in FIG. 30.

Though not specifically illustrated herewith, in some embodiments the locker body can include a spring clip, which is operable to engage the assembly comprising the suture locker. Suitable spring clips can, for example, include those described in U.S. application Ser. No. 11/753,921. Generally, the spring clip can include a spring element that internally projects into the passageway of the locker body. As the pin moves distally, the central section deflects the spring element in a direction toward the interior surface of the front wall. Continued distal movement places the pin in a location distal to the spring element. After the deflection force applied by the central section is removed, the deformed spring element returns to its original undeflected condition, which blocks movement of the pin in the proximal direction and captures the pin in a headspace between the spring element and the cap.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A locker for securing one or more tensioning members, comprising:
   a locker body having a first aperture, a second aperture, and a passageway extending between the first and second apertures, the one or more tensioning members adapted to be threaded through the passageway between the first and second apertures;
   a pull wire that is attached to the locker body and extends proximally therefrom, the pull wire being at least partially disposed within a hollow interior of the locker body and is separated from the one or more tensioning members by a structure that is contained within the hollow interior of the locker body, wherein axial movement of the pull wire is translated into axial movement of the locker body;
   a movable member coupled to the locker body so as to traverse the passageway, the movable member being movable in a direction generally between a first position within the passageway in which the one or more tensioning members are movable relative to the locker body and a second position within the passageway in which the one or more tensioning members are locked relative to the locker body; and
   a hub surrounding the locker body, wherein the locker body is retractable with respect to the hub by moving in a proximal direction relative to the hub such that the movable member is engaged by the hub and moved distally from the first position to the second position in response to a retraction of the locker body with respect to the hub, wherein the movable member remains engaged with the hub in both the first and second positions.

2. The locker of claim 1, wherein the movable member includes end sections extending laterally from the locker body.

3. The locker of claim 2, wherein the hub includes recesses for receiving the end sections of the movable member when the locker body is retracted with respect to the hub.

4. The locker of claim 1 further comprising:
   at least one catheter coupled to the locker body, the at least one catheter being positionable in the vasculature of the patient such that the locker body is proximate a surgical site.

5. The locker of claim 1, wherein the hub remains at a stationary position as the locker body is retracted with respect to the hub.

6. A locker for securing one or more tensioning members, comprising:
   a locker body having a first aperture, a second aperture, and a passageway extending between the first and second apertures, the one or more tensioning members adapted to be threaded through the passageway between the first and second apertures;
   a movable member coupled to the locker body so as to traverse the passageway, the movable member being movable in a direction generally between a latent position within the passageway in which the one or more tensioning members are movable relative to the locker body and an activated position within the passageway in which the one or more tensioning members are locked relative to the locker body;
   a hub surrounding the locker body; and
   a proximally-extending member adapted to extend from the locker body to an incision into the body of a patient, the proximally-extending member operable to retract the locker body with respect to the hub resulting in the locker body moving in a proximal direction relative to the hub and such that the movable member is engaged by the hub and moved distally from the latent position to the activated position in response to a retraction of the locker body with respect to the hub, wherein the movable member remains engaged with the hub in both the latent and activated positions, wherein the proximally-extending member is at least partially disposed within a hollow interior of the locker body and is separated from the one or more tensioning members by a structure that is contained within the hollow interior of the locker body, wherein axial movement of the proximally-extending member is translated into the axial movement of the locker body.

7. The locker of claim 6, wherein the movable member includes end sections extending laterally from the locker body.

8. The locker of claim 7, wherein the hub includes recesses for receiving the end sections of the movable member when the locker body is retracted with respect to the hub, wherein the movable member remains engaged with the recesses of the hub in both the latent and activated positions.

9. The locker of claim 6, wherein the proximally-extending member further comprises at least one of a pull wire or a suture, or a retraction member.

10. The locker of claim 6, wherein a retaining pin couples the proximally-extending member to the locker body.

11. The locker of claim 6 further comprising:
at least one catheter coupled to the locker, the at least one catheter being positionable in the vasculature of the patient such that the locker is proximate a surgical site.

12. The locker of claim 6, wherein the locker includes a wall with a channel, the proximally-extending member extending proximally from the channel.

13. A locker for securing one or more tensioning members, comprising:
a locker body having a first aperture, a second aperture, and a passageway extending between the first and second apertures, the one or more tensioning members adapted to be threaded through the passageway between the first and second apertures, the locker body including a pair of first opposing slots;
a pull wire that is attached to the locker body and extends proximally therefrom, the pull wire being at least partially disposed within a hollow interior of the locker body and is separated from the one or more tensioning members by a structure that is contained within the hollow interior of the locker body, wherein axial movement of the pull wire is translated into the axial movement of the locker body;
a movable member coupled to the locker body so as to traverse the passageway, the movable member being movable in a direction generally between a first position within the passageway in which the one or more tensioning members are movable relative to the locker body and a second position within the passageway in which the one or more tensioning members are locked relative to the locker body;
a hub surrounding the locker body, the hub including a pair of second opposing slots in which ends of the movable member are received, the ends of the movable member passing through the first opposing slots formed in the locker body;
a cap that is coupled to the locker body and closes off distal ends of the first opposing slots to constrain distal movement of the movable member;
wherein the locker body is retractable with respect to the hub by moving in a proximal direction with respect to the hub such that the movable member is engaged by the hub and moved distally from the first position to the second position in response to a retraction of the locker body with respect to the hub, wherein the movable member remains engaged with the hub in both the first and second positions.

14. The locker of claim 13, wherein the movable member includes end sections extending laterally from the locker body.

15. The locker of claim 14, wherein the hub includes recesses for receiving the end sections of the movable member when the locker body is retracted with respect to the hub, wherein the movable member remains engaged with the recesses of the hub in both the first and second positions.

16. The locker of claim 13, wherein a retaining pin couples the pull wire to the locker body.

* * * * *